United States Patent
Chen et al.

(10) Patent No.: US 9,840,525 B2
(45) Date of Patent: Dec. 12, 2017

(54) CRYSTAL FORM OF TENOFOVIR PRODRUG, PREPARATION METHOD THEREOF, AND METHOD OF USE THEREOF

(71) Applicant: Jiangsu Hansoh Pharmaceutical Group Co., Ltd., Lianyungang, Jiangsu (CN)

(72) Inventors: Ming Chen, Lianyungang (CN); Chengyao Tian, Lianyungang (CN); Mingli Zhao, Lianyungang (CN); Jun Yu, Lianyungang (CN); Baohai Yang, Lianyungang (CN); Aifeng Lu, Lianyungang (CN)

(73) Assignee: JIANGSU HANSOH PHARMACEUTICAL GROUP CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 15/326,126

(22) PCT Filed: Jul. 21, 2015

(86) PCT No.: PCT/CN2015/084671
§ 371 (c)(1),
(2) Date: Jan. 13, 2017

(87) PCT Pub. No.: WO2016/011932
PCT Pub. Date: Jan. 28, 2016

(65) Prior Publication Data
US 2017/0204125 A1     Jul. 20, 2017

(30) Foreign Application Priority Data
Jul. 21, 2014   (CN) .......................... 2014 1 0349141

(51) Int. Cl.
*C07F 9/6561*   (2006.01)
*C07C 57/15*    (2006.01)

(52) U.S. Cl.
CPC .......... *C07F 9/65616* (2013.01); *C07C 57/15* (2013.01); *C07B 2200/13* (2013.01)

(58) Field of Classification Search
None
See application file for complete search history.

(56) References Cited

FOREIGN PATENT DOCUMENTS

| CN | 1810816 A | 8/2006 | | |
|---|---|---|---|---|
| CN | 103665043 A | 3/2014 | | |
| CN | CA 2882201 A1 | * | 3/2014 | .......... A61K 31/675 |
| WO | 2013052094 A2 | 4/2013 | | |

OTHER PUBLICATIONS

International Search Report dated Nov. 3, 2015 in International Application No. PCT/CN2015/084671.

* cited by examiner

*Primary Examiner* — Deepak Rao
*Assistant Examiner* — Laura Daniel
(74) *Attorney, Agent, or Firm* — Panitch Schwarze Belisario & Nadel LLP

(57) ABSTRACT

A crystal form of 9-[(R)-2-[[(S)-[[[1-(isopropoxycarbonyl)-1-methyl]ethyl]amino]phenoxyphosphinyl]methoxyl]propyl]adenine fumarate of formula (I) is provided. Also provided is a preparation method and method of using the crystal form. Specifically, a crystal form of 9-[(R)-2-[[(S)-[[[1-(isopropoxycarbonyl)-1-methyl]ethyl]amino]phenoxyphosphinyl]methoxyl]propyl]adenine fumarate of formula (I) having an X-ray powder diffraction (XRPD) spectrum including diffraction peaks at 2θ±0.20° of 5.08, 12.44, 13.18, 22.37, 23.37 and 28.56 is provided. The crystal form provided herein has high bioavailability, significant efficacy, good stability, high yield and high purity, and contributes to the selection and design of a drug administration route and the determination of process parameters of a pharmaceutical preparation, thereby improving drug production quality.

(I)

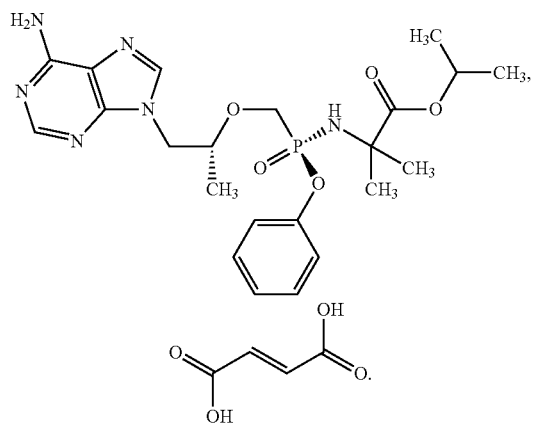

20 Claims, 2 Drawing Sheets

CRYSTAL FORM OF TENOFOVIR PRODRUG, PREPARATION METHOD THEREOF, AND METHOD OF USE THEREOF

CROSS-REFERENCE TO RELATED APPLICATION

This application is a Section 371 of International Application No. PCT/CN2015/084671, filed Jul. 21, 2015, which was published in the Chinese language on Jan. 28, 2016, under International Publication No. WO 2016/011932A1, and the disclosure of which is incorporated herein by reference.

FIELD OF THE INVENTION

The present invention relates to the field of medicinal chemistry, and specifically relates to a new crystal form of a tenofovir prodrug 9-[(R)-2-[[(S)-[[[1-(isopropoxycarbonyl)-1-methyl]ethyl]amino]phenoxyphosphinyl]methoxyl] propyl]adenine fumarate, a preparation method thereof, a pharmaceutical composition comprising a therapeutically effective amount of this compound and medical uses thereof.

BACKGROUND OF THE INVENTION

9-[(R)-2-[[(S)-[[[1-(isopropoxycarbonyl)-1-methyl]ethyl] amino]phenoxyphosphinyl] methoxyl]propyl]adenine fumarate (1) has the following structure:

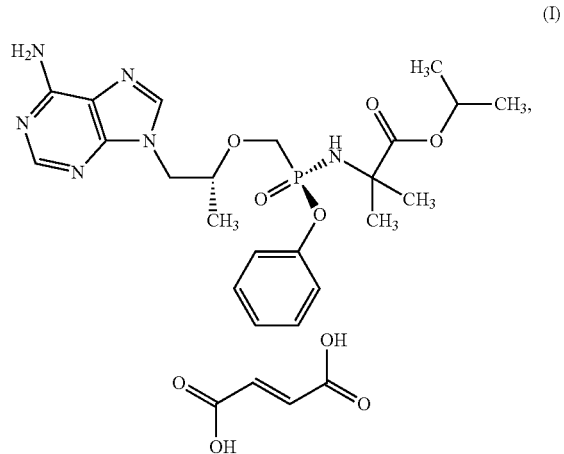

(I)

9-[(R)-2-[[(S)-[[[1-(isopropoxycarbonyl)-1-methyl]ethyl] amino]phenoxyphosphinyl] methoxyl]propyl]adenine fumarate (I) is a nucleoside reverse transcriptase inhibitor and a prodrug of tenofovir (PMPA). PMPA is similar to the natural nucleoside monophosphate in structure and is rapidly transformed into the active metabolite PMPA diphosphate (PMPApp) in the body. PMPApp competes with natural 5' deoxyadenosine triphosphate and is incorporated into the DNA strand of viruses. However PMPApp cannot perform a 5', 3'-phosphodiester bond coupling reaction due to the lack of a 3' OH group, such that DNA strand extension is blocked and replication of the virus is ultimately blocked (FIG. 1). It has been proven that PMPA has anti-human immunodeficiency virus (HIV) activity and anti-hepatitis B virus (HBV) activity.

However, PMPA contains a phosphate group, which is usually negatively charged at physiological pH and the polarity of it is too strong to pass through biological membranes, which leads to poor oral bioavailability, a low tissue distribution coefficient, and a certain nephrotoxicity. Therefore, in the development of such drugs, it is necessary to use the principle of pro-drugs to mask the negative charge of phosphate groups in order to eliminate the drawback of such drugs. A diester prodrug of PMPA, tenofovir disoproxilfumarate (TDF), developed by Gilead company was approved by the U.S. Food and Drug Administration (FDA) in 2001 for the treatment of HIV infection.

TDF has significantly improved the pharmacokinetic properties of PMPA to some extent, but it is rapidly hydrolyzed in the body by non-specific esterases that are widely present in plasma, particularly in the presence of carbonate esterases in intestinal epithelial cells, to release PMPA. High concentrations of PMPA in the plasma are quickly excreted out of the body due to its poor membrane permeability, which leads to difficulty in maintaining adequate concentration at the infected site. In addition, PMPA is the substrate of an organic anion transporter (hOAT) in renal proximal tubule epithelial cells, and the high concentration of PMPA in the plasma easily accumulates in renal proximal tubular epithelial cells, which results in a certain risk of renal toxicity.

A new generation of monophosphonamidate monoester prodrug overcomes the above-mentioned shortcomings of TDF which is very stable in plasma and is not easily hydrolyzed by esterases. When it is absorbed into the cells, it is immediately transformed into PMPA in the presence of serine proteases (cathepsinA) and specific amidases. Therefore, it has a better tissue permeability and lymphoid tissue and cell targeting. The monophosphonamidate monoester prodrug GS7340 (refer to PCT patent application WO2013052094 A2) developed by Gilead company has successfully entered into phase III clinical trials, and the results show that GS7340 has a stronger anti-virus capability and better safety in comparison to 30 times the dose of TDF.

9-[(R)-2-[[(S)-[[[1-(isopropoxycarbonyl)-1-methyl]ethyl] amino]phenoxyphosphinyl]methoxyl]propyl]adenine fumarate (1), like GS7340, can release the active ingredient PMPA in cells. Its auxiliary group is cleverly designed, with its structure being different from GS7340 in only a single methyl group, and the removing mechanism and manner of the auxiliary group in cells is also almost the same as those of GS7340. It can be expected that HS-10234, due to its advantages in absorption and distribution, will be more effective than TDF and other prodrugs in improving the efficacy of the active ingredient PMPA. As the most promising new generation of PMPA prodrugs, HS-10234 will benefit the majority of patients.

It is known to the person skilled in the art that the polymorphic form of a drug has become an essential pan of the pharmaceutical research process and the quality control and detection of the finished drug product. The study of drug polymorphism is beneficial to selecting the bioactivity of a new drug compound, to improving the bioavailability, to improving the clinical curative effect, to selecting and designing the drug administration route, and to determining the parameters of the pharmaceutical preparation process, thereby improving the quality of drug production. The bioavailability may be significantly different among different crystal forms for the same drug. For one drug, some crystal forms may have higher biological activity than other crystal forms. To provide a crystal form of tenofovir prodrug with higher bioactivity and more suitable medical application is a technical problem that the medical field has been looking forward to solving.

SUMMARY OF THE INVENTION

The object of the present invention is to solve the above technical problem, and to provide a new crystal form of tenofovir prodrug 9-[(R)-2-[[(S)-[[[1-(isopropoxycarbonyl)-1-methyl]ethyl]amino]phenoxyphosphinyl]methoxyl]propyl]adenine fumarate which is named as crystal form A in the present invention.

The XRPD spectrum of crystal form A according to the present invention comprises at least diffraction peaks at 2θ±0.20° of 5.08, 12.44, 13.18, 22.37, 23.37 and 28.56.

Preferably, the XRPD spectrum of crystal form A of 9-[(R)-2-[[(S)-[[[1-(isopropoxycarbonyl)-1-methyl]ethyl]amino]phenoxyphosphinyl]methoxy]propyl]adenine fumarate comprises at least diffraction peaks at 2θ±0.200 of 5.08, 7.42, 10.15, 12.44, 13.18, 22.37, 23.37, and 28.56, more preferably further comprises diffraction peaks at 2θ±0.20° of 16.35, 18.23, 21.36, 25.00, and 31.68.

Particularly preferred, the XRPD spectrum of crystal form A is as shown in FIG. 1.

The result of differential thermal analysis of crystal form A of 9-[(R)-2-[[(S)-[[[1-(isopropoxycarbonyl)-1-methyl]ethyl]amino]phenoxyphosphinyl]methoxy]propyl]adenine fumarate according to the present invention shows a sharp endothermic melting peak at 110.9° C.

Another object of the present invention is to provide a method for preparing crystal form A of 9-[(R)-2-[(S)-[[[1-(isopropoxycarbonyl)-1-methyl]ethyl]amino]phenoxyphosphinyl]methoxy]propyl]adenine fumarate, comprising the following steps of:

(1) dissolving any forms of 9-[(R)-2-[(S)-[[[1-(isopropoxycarbonyl)-1-methyl]ethyl]amino]phenoxyphosphinyl]methoxy]propyl]adenine fumarate into an organic solvent under heating;

(2) cooling the solution of 9-[(R)-2-[(S)-[[[1-(isopropoxycarbonyl)-1-methyl]ethyl]amino]phenoxyphosphinyl]methoxy]propyl]adenine fumarate to precipitate a crystal; and (3) filtering out the crystal to obtain crystal form A.

Preferably, the organic solvent is selected from the group consisting of acetonitrile, anhydrous methanol, anhydrous ethanol, isopropanol, anhydrous methanol/n-heptane, anhydrous ethanol/n-heptane, isopropanol/n-heptane, anhydrous methanol/methyl tert-butyl ether, anhydrous ethanol/methyl tert-butyl ether, isopropanol/methyl tert-butyl ether, anhydrous methanol/isopropyl ether, anhydrous ethanol/isopropyl ether, isopropanol/isopropyl ether, anhydrous methanol/diethyl ether, anhydrous ethanol/diethyl ether and isopropanol/diethyl ether, more preferably anhydrous methanol/n-heptane.

Preferably, the temperature of heating the organic solvent is generally from 30° C. to the reflux temperature, preferably the reflux temperature; and the crystallization temperature is preferably −40 to 40° C., most preferably 0° C. to 10° C.

A further object of the present invention is to provide a pharmaceutical composition comprising an effective amount of said crystal form A, optionally, the pharmaceutical composition further comprises a pharmaceutically acceptable carrier.

The composition according to the present invention is administered via a suitable route comprising oral route and injection route etc., preferably oral route. Suitable dosage forms include tablets, capsules, dispersions and suspensions, preferably tablets.

Another object of the present invention is to provide a use of said crystal form A and the pharmaceutical composition comprising crystal form A in the preparation of a medicament for the treatment of AIDS or hepatitis B virus.

The new crystal form A according to the present invention has the advantages of high bioavailability, remarkable efficacy, good stability, high yield and high purity etc. The new crystal form according to the present invention is beneficial to selecting and designing the drug administration route, and to determining the parameters of the pharmaceutical preparation process, thereby improving the quality of the drug production.

DETAILED DESCRIPTION OF THE INVENTION

In order to illustrate the technical solution of the present invention and the effect obtained thereby, the present invention will be further described with reference to the specific examples below, but it will be appreciated that the scope of the present invention is not limited to these specific examples.

Example 1

5.0 g of 9-[(R)-2-[(S)-[[[1-(isopropoxycarbonyl)-1-methyl]ethyl]amino]phenoxyphosphinyl]methoxy]propyl]adenine fumarate, 20.0 ml of anhydrous methanol and 5 ml of n-heptane were placed in a reaction flask and then heated to reflux until the solid was completely dissolved. The heating was stopped and the solution was cooled to 0 to 10° C. and stirred for 2 hours to precipitate a crystal. The solid was filtered out to obtain crystal form A.

Figure 1:
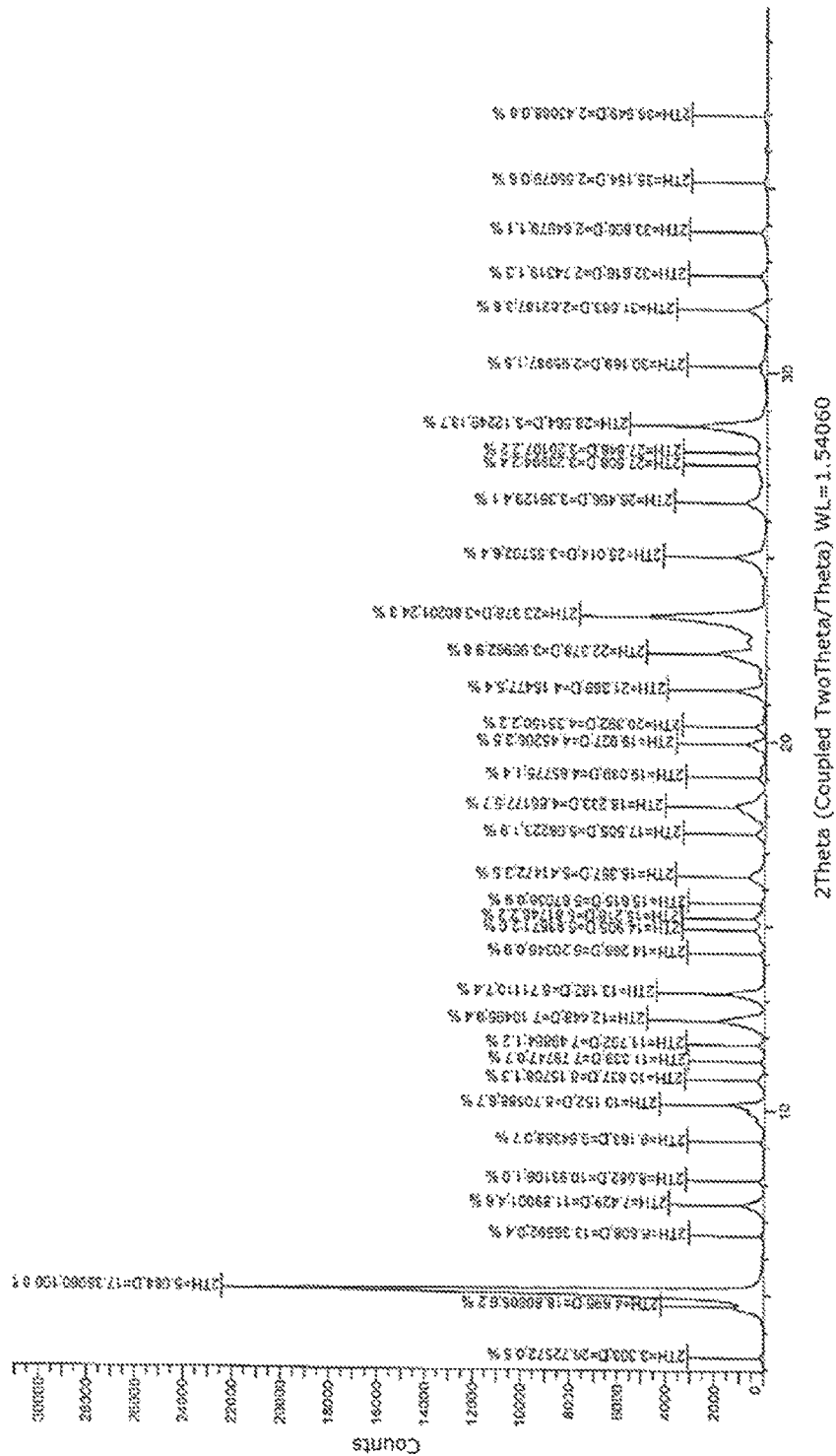
FIG. 1 is the X-ray powder diffraction (XRPD) spectrum of the new crystal form of 9-[(R)-2-[(S)-[[[1-(isopropoxycarbonyl)-1-methyl]ethyl]amino]phenoxyphosphinyl]methoxy]propyl]adenine fumarate according to the present invention.
Figure 2:
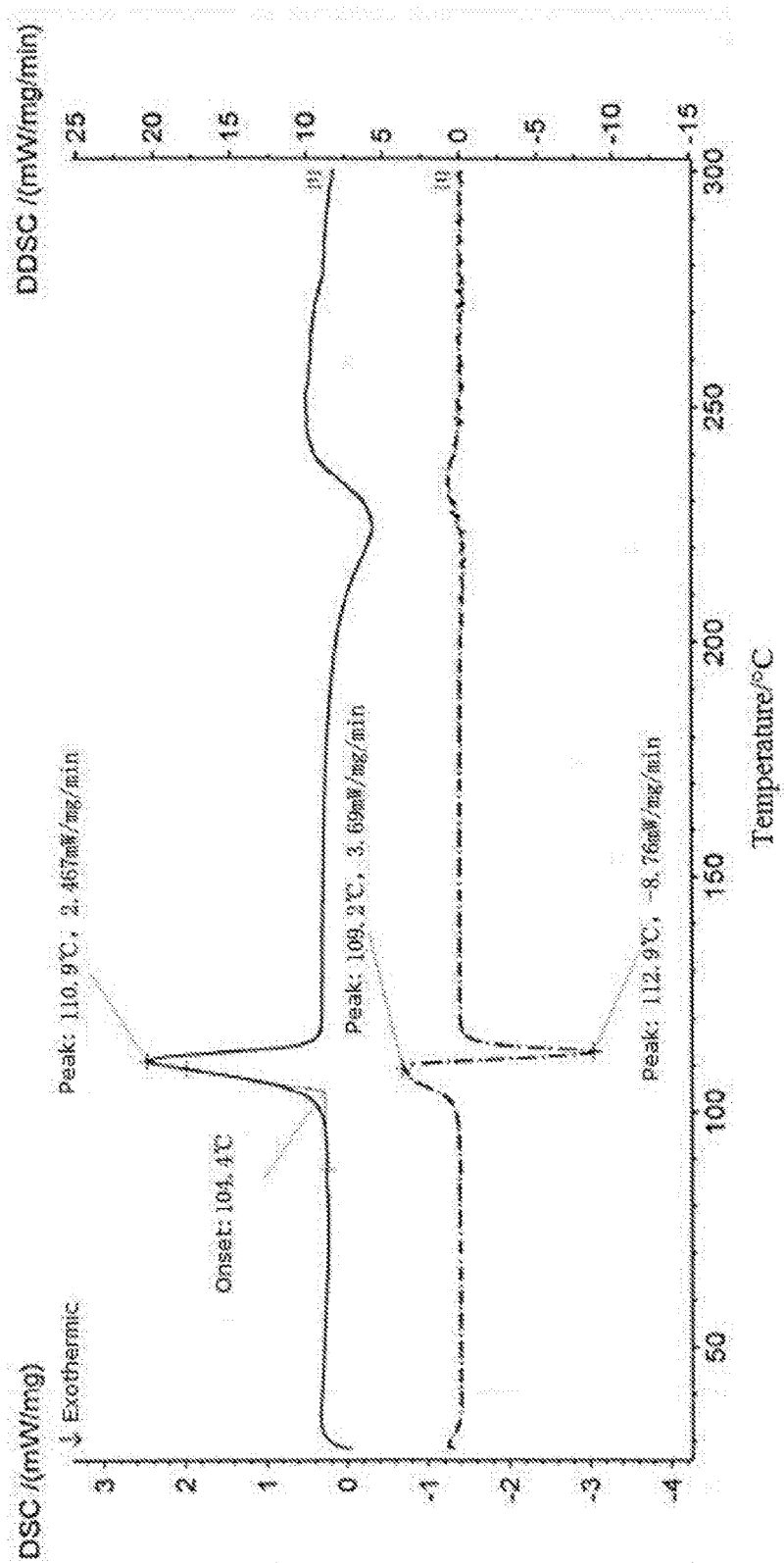
FIG. 2 is the differential scanning calorimetry (DSC) spectrum of the new crystal form of 9-[(R)-2-[(S)-[[[1-(isopropoxycarbonyl)-1-methyl]ethyl]amino]phenoxyphosphinyl]methoxy]propyl]adenine fumarate according to the present invention.

After testing and verification, its X-ray powder diffraction spectrum was as shown in FIG. 1, and its DSC spectrum was consistent with FIG. 2, which demonstrated that the resulting crystal form was crystal form A.

Example 2

5.0 g of 9-[(R)-2-[(S)-[[[1-(isopropoxycarbonyl)-1-methyl]ethyl]amino]phenoxyphosphinyl]methoxy]propyl]adenine fumarate and 20.0 ml of anhydrous ethanol were placed in a reaction flask and then heated to reflux until the solid was completely dissolved. The heating was stopped and the solution was cooled to 0 to 10° C. and stirred for 2 hours to precipitate a crystal. The solid was filtered out to obtain crystal form A.

After testing and verification, its X-ray powder diffraction spectrum was consistent with FIG. 1, and its DSC spectrum was consistent with FIG. 2, which demonstrated that the resulting crystal form was crystal form A.

Example 3

5.0 g of 9-[(R)-2-[(S)-[[[1-(isopropoxycarbonyl)-1-methyl]ethyl]amino]phenoxyphosphinyl]methoxy]propyl]adenine fumarate, 20.0 ml of isopropanol and 5 ml of methyl tert-butyl ether were placed in a reaction flask and then heated to reflux until the solid was completely dissolved. The heating was stopped and the solution was cooled to 0 to 10° C. and stirred for 2 hours to precipitate a crystal. The solid was filtered out to obtain crystal form A.

After testing and verification, its X-ray powder diffraction spectrum was consistent with FIG. 1, and its DSC spectrum was consistent with FIG. 2, which demonstrated that the resulting crystal form was crystal form A.

Experimental Example

Stability Study

The stability of the new crystal form prepared by the method of Example 1 of the present invention was studied. The results showed that the new crystal form A of the present invention did not undergo transformation in the stability test and did not undergo chemical degradation, which was stable at room temperature and in line with the drug and preparation requirements. The details are shown in the table below:

| Conditions | Appearance | | Product Purity | Crystal Form |
|---|---|---|---|---|
| 30° C. ± 2° C./RH 65% ± 5% | 0 month | off-white powder | 98.97% | Crystal form A |
| | 3 months | off-white powder | 98.95% | Crystal form A |
| | 6 months | off-white powder | 98.92% | Crystal form A |

Experimental Example

Flowability Study

The flowability of the new crystal form prepared in Examples 1, 2 and 3 of the present invention was studied. The results showed that the new crystal form A of the present invention had good flowability.

| | Example 1 | Example 2 | Example 3 |
|---|---|---|---|
| Repose Angle | 36° | 35° | 34° |

Experimental Example

Determination of Absolute Bioavailability

The absolute bioavailability of the new crystal form A prepared according to the present invention as measured by intravenous administration and oral administration in rats was as high as 81%. The results showed that the new crystal form prepared according to the present invention had high bioavailability.

What is claimed is:

1. A crystal form of 9-[(R)-2-[[(S)-[[[1-(isopropoxycarbonyl)-1-methyl]ethyl]amino]phenoxyphosphinyl]methoxy]propyl]adenine fumarate of formula (I):

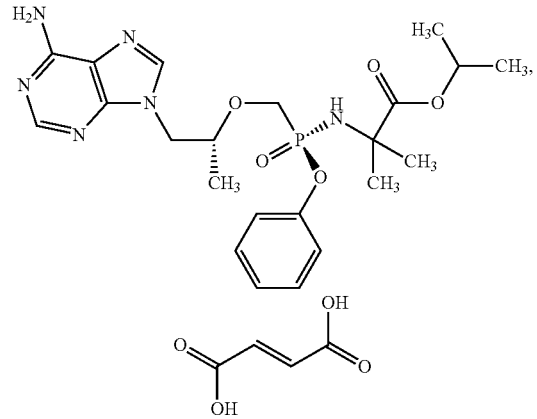

(I)

the crystal form having a characteristic X-ray powder diffraction (XRPD) spectrum comprising diffraction peaks at 2θ±0.20° of 5.08, 12.44, 13.18, 22.37, 23.37, and 28.56.

2. The crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 1, wherein the XRPD spectrum comprises diffraction peaks at 2θ±0.20° of 5.08, 7.42, 10.15, 12.44, 13.18, 22.37, 23.37, and 28.56.

3. The crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 1, wherein the crystal form has a differential scanning calorimetry (DSC) spectrum comprising an endothermic melting peak at 110.9 ° C.

4. The crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 1, having an XRPD spectrum as shown in FIG. 1.

5. A preparation method of the crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 1, wherein the preparation method comprises:
(a) dissolving any form of 9-[(R)-2-[(S)-[[[1-(isopropoxycarbonyl)-1-methyl]ethyl]amino]phenoxyphosphinyl]methoxy]propyl]adenine fumarate in an organic solvent under heating to obtain a solution of 9-[(R)-2-[(S)-[[[1-(isopropoxycarbonyl)-1-methyl]ethyl]amino]phenoxyphosphinyl]methoxy]propyl]adenine fumarate;
(b) cooling the solution of 9-[(R)-2-[(S)-[[[1-(isopropoxycarbonyl)-1-methyl]ethyl]amino]phenoxyphosphinyl]methoxy]propyl]adenine fumarate to precipitate a crystal; and
(c) filtering the crystal to obtain the target crystal form.

6. The preparation method according to claim 5, wherein the organic solvent is selected from the group consisting of acetonitrile, anhydrous methanol, anhydrous ethanol, isopropanol, anhydrous methanol/n-heptane, anhydrous ethanol/n-heptane, isopropanol/n-heptane, anhydrous methanol/methyl tert-butyl ether, anhydrous ethanol/methyl tert-butyl ether, isopropanol/methyl tert-butyl ether, anhydrous methanol/isopropyl ether, anhydrous ethanol/isopropyl ether, isopropanol/isopropyl ether, anhydrous methanol/diethyl ether, anhydrous ethanol/diethyl ether and isopropanol/diethyl ether.

7. The preparation method according to claim 5, wherein the 9-[(R)-2-[(S)-[[[1-(isopropoxycarbonyl)-1-methyl]ethyl]amino]phenoxyphosphinyl]methoxy]propyl]adenine fumarate is dissolved in the organic solvent at a temperature of 30° C. to a reflux temperature.

8. The preparation method according to claim 5, wherein the solution of 9-[(R)-2-[(S)-[[[1-(isopropoxycarbonyl)-1-methyl]ethyl]amino]phenoxyphosphinyl]methoxy]propyl]adenine fumarate is cooled to a temperature of −40° C. to 40° C.

9. A pharmaceutical composition comprising the crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 1, optionally further comprising a pharmaceutically acceptable carrier.

10. The pharmaceutical composition according to claim 9, wherein the composition is formulated for oral administration or injection.

11. The pharmaceutical composition according to claim 9, wherein the composition is formulated as a tablet, capsule, dispersion or suspension.

12. The crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 2, wherein the XRPD spectrum further comprises diffraction peaks at 2θ±0.20° of 16.35, 18.23, 21.36, 25.00, and 31.68.

13. The preparation method according to claim 6, wherein the organic solvent is anhydrous methanol/n-heptane.

14. The preparation method according to claim 7, wherein the temperature is the reflux temperature.

15. The preparation method according to claim 8, wherein the temperature is 0° C. to 10° C.

16. The pharmaceutical composition according to claim 10, being formulated for oral administration.

17. The pharmaceutical composition according to claim 11, being formulated as a tablet.

18. A pharmaceutical composition comprising the crystal form of 9-[(R)-2-[[(S)-[[[1-(isopropoxycarbonyl)-1-methyl]ethyl]amino]phenoxyphosphinyl]methoxy]propyl]adenine fumarate of formula (I) according to claim 4, optionally further comprising a pharmaceutically acceptable carrier.

19. A method of treating acquired immune deficiency syndrome (AIDS) or hepatitis B virus (HBV) in a subject in need thereof, the method comprising administering to the subject the pharmaceutical composition according to claim 9.

20. A method of treating acquired immune deficiency syndrome (AIDS) or hepatitis B virus (HBV) in a subject in need thereof, the method comprising administering to the subject the pharmaceutical composition according to claim 18.

* * * * *